US010537297B2

(12) United States Patent
Hagiwara (10) Patent No.: US 10,537,297 B2
(45) Date of Patent: Jan. 21, 2020

(54) RADIATION TOMOGRAPHY APPARATUS AND PROGRAM FOR CARDIAC-GATED IMAGING

(71) Applicant: General Electric Company, Schenectady, NY (US)

(72) Inventor: Akira Hagiwara, Tokyo (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/514,895

(22) PCT Filed: Sep. 18, 2015

(86) PCT No.: PCT/US2015/050902
§ 371 (c)(1),
(2) Date: Mar. 28, 2017

(87) PCT Pub. No.: WO2016/053644
PCT Pub. Date: Apr. 7, 2016

(65) Prior Publication Data
US 2017/0238893 A1 Aug. 24, 2017

(30) Foreign Application Priority Data
Sep. 30, 2014 (JP) .................................. 2014-200729

(51) Int. Cl.
*A61B 6/00* (2006.01)
*A61B 6/03* (2006.01)
*A61B 6/02* (2006.01)

(52) U.S. Cl.
CPC .............. *A61B 6/503* (2013.01); *A61B 6/00* (2013.01); *A61B 6/02* (2013.01); *A61B 6/032* (2013.01); *A61B 6/54* (2013.01); *A61B 6/541* (2013.01)

(58) Field of Classification Search
None
See application file for complete search history.

(56) References Cited

U.S. PATENT DOCUMENTS 4,398,251 A * 8/1983 LeMay .................. A61B 6/032
128/922
6,118,839 A * 9/2000 Dafni ..................... A61B 6/032
378/15

(Continued)

FOREIGN PATENT DOCUMENTS

JP    2001076169 A    3/2001
JP    2004202246 A    7/2004

(Continued)

OTHER PUBLICATIONS

Japanese Search Report issued in connection with corresponding JP Application No. 2014-200729 dated May 23, 2017.

(Continued)

*Primary Examiner* — Samah A Beg (57) ABSTRACT

A radiation tomography system is provided that includes a control unit to control a data collection system to acquire first data by scanning a first scan region centered on a first position in a body axis direction of a subject in synchronization with heartbeats, and second data by scanning a second scan region adjacent to the first scan region and centered on a second position in the body axis direction in synchronization with the heartbeats. A reconstructing unit is provided to reconstruct an image of a slice between the first position and second positions using the first and second data. The reconstructing unit determines a view-angle-range-based use rate for the first data and a view-angle-range-based use rate for the second data according to the position of the slice relative to the first and second positions.

9 Claims, 11 Drawing Sheets

(56) References Cited

U.S. PATENT DOCUMENTS

| | | | | |
|---|---|---|---|---|
| 6,252,926 B1* | 6/2001 | Flohr | G06T 11/005 | 378/15 |
| 6,324,246 B1* | 11/2001 | Ruimi | A61B 6/032 | 378/15 |
| 6,415,012 B1* | 7/2002 | Taguchi | A61B 6/032 | 378/15 |
| 6,421,411 B1* | 7/2002 | Hsieh | A61B 6/032 | 378/19 |
| 6,826,251 B1* | 11/2004 | Miyazaki | A61B 6/027 | 378/15 |
| 6,865,250 B2 | 3/2005 | Londt et al. | | |
| 6,870,898 B1* | 3/2005 | von der Haar | A61B 6/032 | 378/97 |
| 9,378,567 B2* | 6/2016 | Hagiwara | G06T 11/005 | |
| 9,861,332 B2* | 1/2018 | Fukuda | A61B 6/5205 | |
| 9,949,706 B2* | 4/2018 | Fukuda | A61B 6/5235 | |
| 2002/0118790 A1 | 8/2002 | Pan et al. | | |
| 2003/0123603 A1* | 7/2003 | Suzuki | A61B 6/032 | 378/4 |
| 2005/0123091 A1* | 6/2005 | Nishide | G06T 11/006 | 378/19 |
| 2005/0175143 A1* | 8/2005 | Miyazaki | A61B 6/032 | 378/19 |
| 2006/0198490 A1* | 9/2006 | Tsuyuki | A61B 6/032 | 378/8 |
| 2006/0274878 A1* | 12/2006 | Hsieh | A61B 6/0457 | 378/8 |
| 2006/0280283 A1* | 12/2006 | Hsieh | A61B 6/032 | 378/8 |
| 2007/0053480 A1* | 3/2007 | Nishide | A61B 6/00 | 378/4 |
| 2007/0121780 A1* | 5/2007 | Watanabe | A61B 6/032 | 378/8 |
| 2008/0101531 A1* | 5/2008 | Seamans | A61B 6/541 | 378/8 |
| 2008/0101532 A1* | 5/2008 | Tkaczyk | A61B 6/541 | 378/8 |
| 2009/0110139 A1* | 4/2009 | Noshi | A61B 6/032 | 378/4 |
| 2009/0110256 A1* | 4/2009 | Thielemans | A61B 6/032 | 382/131 |
| 2011/0142313 A1* | 6/2011 | Pack | G06T 11/005 | 382/131 |
| 2011/0255657 A1* | 10/2011 | Noordhoek | A61B 6/032 | 378/11 |
| 2012/0106695 A1* | 5/2012 | Fan | A61B 6/4085 | 378/8 |
| 2012/0189158 A1* | 7/2012 | Berman | G06T 11/006 | 382/100 |
| 2012/0308102 A1* | 12/2012 | Pack | G06T 11/006 | 382/131 |
| 2013/0028498 A1* | 1/2013 | Dennerlein | G01N 23/046 | 382/132 |
| 2013/0251229 A1* | 9/2013 | Ramirez Giraldo | G06T 11/003 | 382/131 |
| 2014/0016847 A1* | 1/2014 | Nett | G06T 11/008 | 382/131 |
| 2017/0091962 A1* | 3/2017 | Hagiwara | A61B 6/032 | |
| 2017/0273656 A1* | 9/2017 | Hagiwara | A61B 6/027 | |

FOREIGN PATENT DOCUMENTS

| | | |
|---|---|---|
| JP | 2009056229 A | 3/2009 |
| JP | 2010075553 A | 4/2010 |

OTHER PUBLICATIONS

Office Action issued in connection with corresponding JP Application No. 2014-200729 dated Jun. 6, 2017.

International Search Report and Written Opinion for corresponding PCT application No. PCT/US2015/050902 dated Dec. 23, 2015; 11 pages.

* cited by examiner

RADIATION TOMOGRAPHY APPARATUS AND PROGRAM FOR CARDIAC-GATED IMAGING

CROSS-REFERENCE TO RELATED APPLICATIONS

This is a national stage application under 35 U.S.C. § 371(c) of PCT Application No. PCT/US2015/050902, filed on Sep. 18, 2015, which claims priority to Japanese Application No. 2014-200729, filed on Sep. 30, 2014, the disclosures of which are incorporated herein by reference in their entireties.

BACKGROUND

The present invention relates to a technique for imaging an object to be imaged in synchronization with heartbeats by a radiation tomography apparatus.

One known imaging technique by a radiation tomography apparatus is cardiac-gated imaging in which a heart is an object to be imaged. In the cardiac-gated imaging, a scan is performed targeting a period of time in which a change of the heart is small in each cardiac cycle, and such a scan is repetitively performed a plurality of number of times while shifting the scan region to scan the whole imaging range including the heart. Based on the thus-acquired scan data, image reconstruction is performed for several slices in the imaging range. More particularly, this is achieved by the following procedure, for example.

First, a heart rate monitor such as an electrocardiograph is used to measure the heartbeat waveform of a subject nearly in real time. A reference time for a scan is defined at about 70-% cardiac phase, which is generally equivalent to the middle of diastole of the heart, wherein the cardiac phase is defined as 0% to 100% from one R-wave to the next R-wave in the heartbeat waveform. The reference time is a time serving as reference of a period of time for collecting scan data over a gantry rotation angle i.e., a view angle, required in image reconstruction. Then, a scan is performed on part of the imaging range, which is a scan region, over a certain time span, for example, in a period of time of the order of 0.24 seconds, centering on the reference time. This scan is repetitively performed over a plurality of heartbeats while shifting the scan region for each heartbeat, and the whole imaging range is thus scanned.

At that time, only one scan reference time is defined in one cardiac cycle. The mode of scanning is an axial scan, or a helical scan with low helical pitch, for example, a helical pitch of 0.2 or lower. Moreover, data collection by the scan on a heartbeat-by-heartbeat basis is achieved by employing a half scan technique that collects scan data in a view angle range of 180 degrees plus a radiation fan beam angle so that temporal resolution comes first is disclosed in Patent Document 1 (Japanese Patent Application KOKAI No. 2004-202246). The half scan technique is also referred to as segment scan technique or partial scan technique. These are reasonable conditions considering the facts that: an actual cardiac cycle, i.e., an R-R interval, is of the order of 0.75 to 1.2 seconds and a period of small change in which motion of the heart is small, for example, diastole, occupies around 25% of the cardiac cycle; the upper limit of the velocity of gantry rotation is currently of the order of 0.35 seconds/rotation; and extremely high-speed movement of a table on which the subject is laid is impractical.

Moreover, image reconstruction is performed for a unit based on the defined reference time. Specifically, from scan data collected by one heartbeat-based scan, image reconstruction only for a slice in a scan region at that time is performed. This is because the object to be imaged is a heart, which is an anatomical part moving relatively fast and in a complicated manner, and hence, respective periods of collection of data used in image reconstruction of several slices are aligned with one another as much as possible to prevent variation of the data from appearing on reconstructed images of the slices arranged in the body axis direction.

Figure 10:
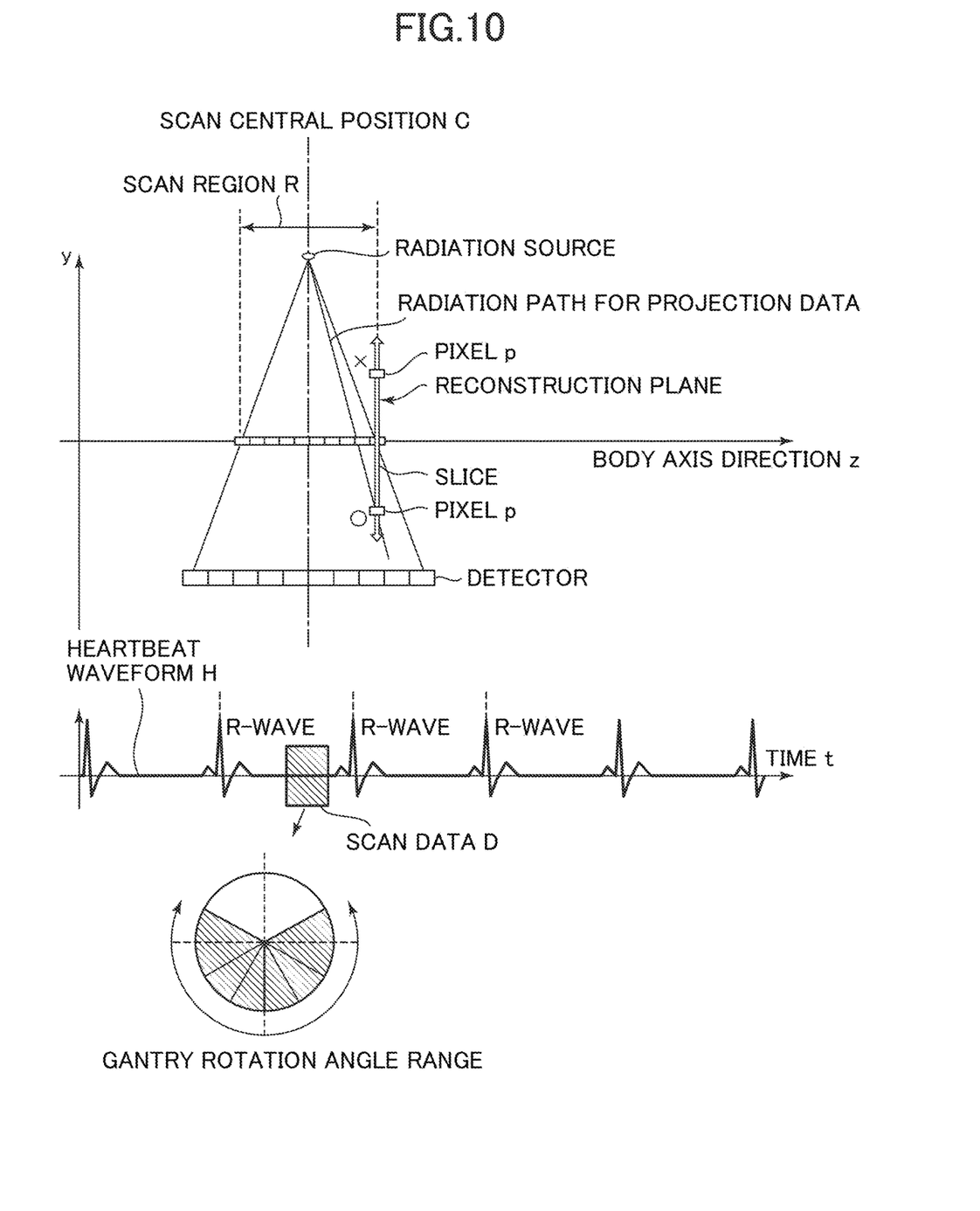
FIG. 10 is a first diagram for explaining a problem in conventional cardiac-gated imaging.
Figure 11:
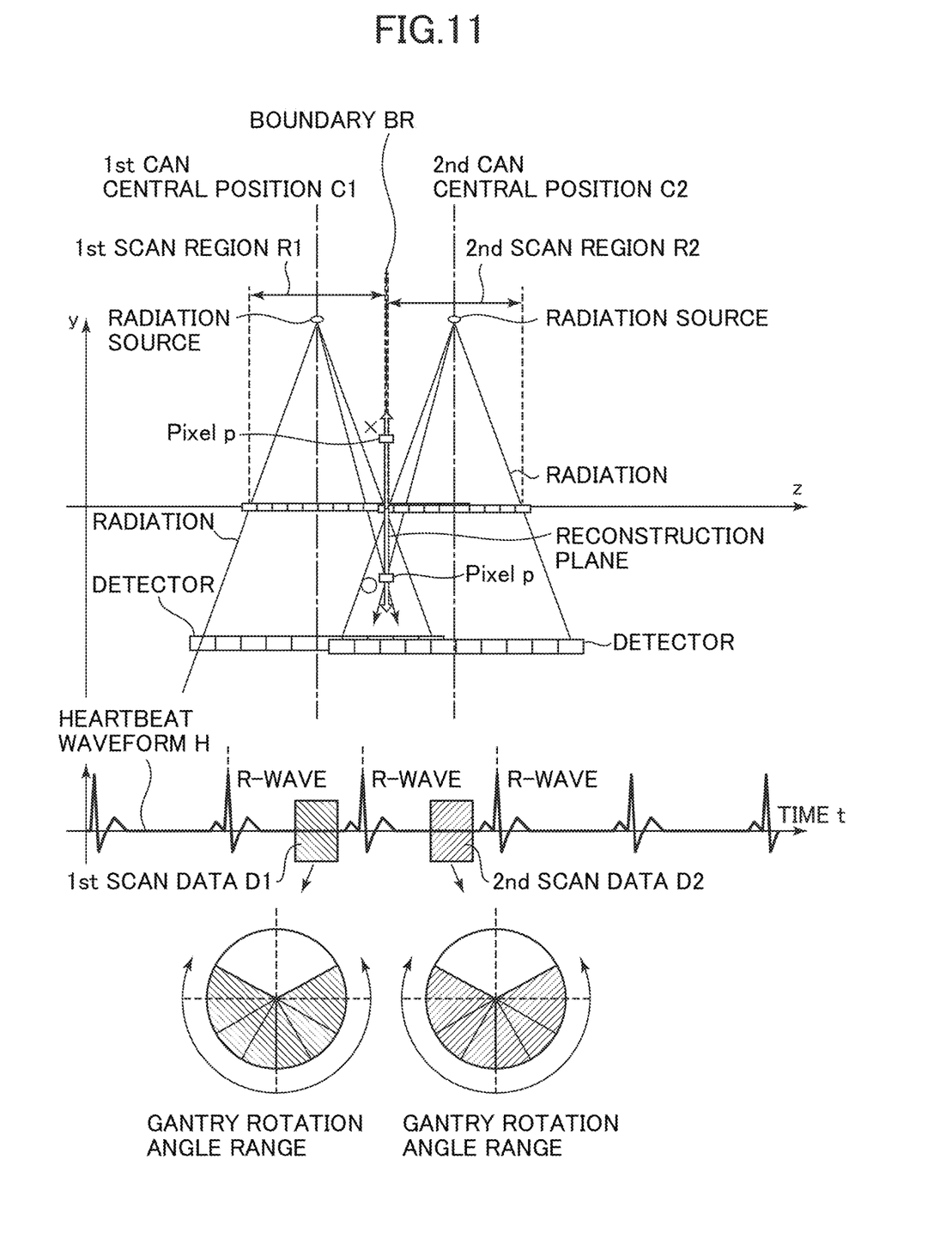
FIG. 11 is a second diagram for explaining the problem in the conventional cardiac-gated imaging.

Furthermore, the scan region in the heartbeat-based scan is defined so that the regions for the temporally adjacent scans partially overlap one another. The reason thereof is as follows: in the case that a half scan is performed for the heartbeat-based scan, image reconstruction based on scan data therefrom results in insufficiency of projection data that lie substantially mutually opposite in a direction of a reconstruction plane of the slice (referred to hereinbelow as conjugate data), leading to generation of a missing cone region having no data in some region in the vicinity of either end in the slice direction (z-axis direction) of the detector during the scan, as shown in FIG. 10. Thus, noticeable cone-beam artifacts appear in reconstructed images of such slices in the vicinity of either end. Accordingly, from scan data of a half scan within one cardiac cycle, image reconstruction only for a region slightly inward of its scan region is performed. Specifically, as shown in FIG. 11, a scan region in the heartbeat-based scan is defined so that adjacent scan regions partially overlap one another. Thus, in conventional cardiac-gated imaging, adjacent scan regions are defined to partially overlap one another in order to reduce disadvantages from application of a half scan.

Nevertheless, there is still found a missing cone in the vicinity of either end for each scan region depending upon the conditions, leading to generation of cone-beam artifacts in reconstructed images of slices in the vicinity of either end of the region. Therefore, when a three-dimensional image is produced by stacking in the body axis direction reconstructed images of slices lying at positions in the body axis direction, boundary artifacts occur in the vicinity of the border between the scan regions.

One method for solving this problem is a method involving correcting an image in the vicinity of a border between adjacent scan regions by referring to reconstructed images of nearby slices which is disclosed in Patent Document 2 (Japanese Patent Application KOKAI No. 2001-076169), or producing these reconstructed images by simply or adaptively combining them so that discontinuity of the images is thereby reduced. For example, an image in the vicinity of a border between scan regions is produced by applying weighted addition to a reconstructed image of a slice closer to one side of the vicinity and that of a slice closer to the other in a proportion of 1:1.

SUMMARY OF INVENTION

However, there is generally present a risk that correction in an image space or simple mixing of images leads to degradation of spatial resolution, thus resulting in a blurred image.

In such circumstances, there is a need for a technique capable of reducing, in an image obtained in cardiac-gated imaging by a radiation tomography apparatus, boundary artifacts while suppressing degradation of spatial resolution.

In a first aspect, there is provided a radiation tomography apparatus for performing cardiac-gated imaging on a subject using a data collection system comprising a radiation source and a detector rotating around said subject, said radiation tomography apparatus comprising a control means for controlling said data collection system to acquire first scan data by a first scan for scanning a first scan region centering on a first position of said subject in a body axis direction in synchronization with heartbeats of said subject, and acquire second scan data by a second scan for scanning a second scan region adjacent to or partially overlapping said first scan region and centering on a second position in said body axis direction in synchronization with said heartbeats; and a reconstructing means for reconstructing an image corresponding to a slice between said first position and said second position using said first and second scan data, said reconstructing means determining a view-angle-range-based use rate for said first scan data and a view-angle-range-based use rate for said second scan data according to a position of said slice relative to said first and second positions.

In a second aspect, there is provided the radiation tomography apparatus in the first aspect, wherein said reconstructing means lowers the view-angle-range-based use rate for said second scan data for a position of said slice closer to said first position, and lowers the view-angle-range-based use rate for said first scan data for a position of said slice closer to said second position.

In a third aspect, there is provided the radiation tomography apparatus in the first or second aspect, wherein when reconstructing a pixel in a reconstruction plane of said slice by back-projecting scan data for a radiation path passing through said pixel, said reconstructing means changes a weight of said scan data according to an angle of said radiation path with respect to said reconstruction plane.

In a fourth aspect, there is provided the radiation tomography apparatus in the third aspect, wherein said reconstructing means increases the weight of scan data for said radiation path for a smaller angle of said radiation path with respect to said reconstruction plane, and decreases the weight of the scan data for said radiation path for a larger said angle.

In a fifth aspect, there is provided the radiation tomography apparatus in any one of the first through fourth aspects, wherein said first and second scans each acquire scan data in a view angle range of 180 degrees plus a radiation fan beam angle, and said control means controls said data collection system so that a difference between a central angle of the view angle range in said first scan and a central angle of the view angle range in said second scan is 90 degrees or more.

In its sixth aspect, the present invention provides the radiation tomography apparatus in the fifth aspect, wherein said control means controls said data collection system so that said difference is substantially 180 degrees.

In its seventh aspect, the present invention provides the radiation tomography apparatus in the sixth aspect, wherein said reconstructing means reconstructs an image corresponding to said slice using scan data in a view angle range of 360 degrees.

In its eighth aspect, the present invention provides a program for causing a computer to function as several sections in the radiation tomography apparatus in any one of the first through seventh aspects.

The "data collection system" comprises a radiation source, a detector, and a gantry for mounting them, for example.

The "scan data" refers to projection data, for example.

According to the invention in the aspects described above, in cardiac-gated imaging in which a scan in synchronization with heartbeats is repetitively performed a plurality of number of times while shifting a scan region in the scan, an image corresponding to a slice at each position within a region including a virtual border between a first scan region and a second scan region that are adjacent to each other in a body axis direction of a subject is reconstructed using first scan data acquired by a scan on the first scan region and second scan data acquired by a scan on the second scan region, wherein a view-angle-range-based use rate for the first scan data and a view-angle-range-based use rate for the second scan data are determined according to the position of that slice relative to respective center positions of the first and second scan regions; therefore, images can be continuously changed centering on an image at the border between the first scan region and second scan region toward images away from the border to reduce artifacts due to discontinuous boundaries. Moreover, since the processing of obtaining images can mix complementary scan data together so that insufficiency of scan data due to a missing cone is complemented, rather than simply mixing images, and then reconstruct images based on the scan data, the images are less susceptible to what is commonly called blurring. As a result, it is possible to reduce boundary artifacts while suppressing degradation of spatial resolution in an image obtained in cardiac-gated imaging by a radiation tomography apparatus.

DETAILED DESCRIPTION

Description of Embodiment

Now an embodiment of the invention will be described. It should be noted that the invention is not limited thereto.

First, a configuration of an X-ray CT (Computed Tomography) apparatus in accordance with the present embodiment will be described.

Figure 1:
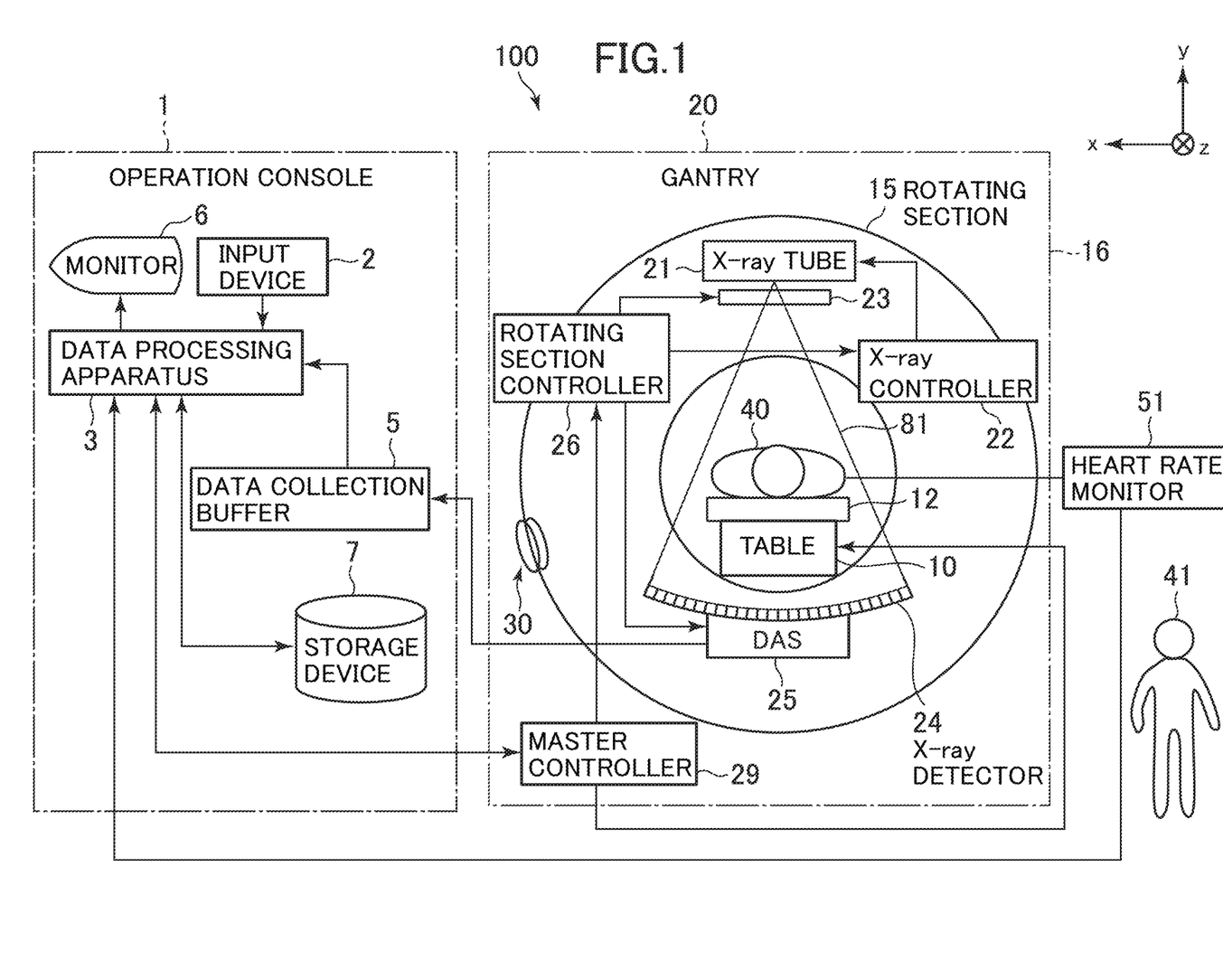
FIG. 1 is a diagram schematically showing a configuration of an X-ray CT apparatus in accordance with an embodiment of the invention.

FIG. 1 is a diagram schematically showing a configuration of an X-ray CT apparatus in accordance with the present embodiment.

As shown in FIG. 1, an X-ray CT apparatus 100 comprises an operation console 1, a table 10, and a gantry 20.

The operation console 1 comprises an input device 2 for accepting an input from an operator 41, a data processing apparatus 3 for performing control of several sections for scanning a subject 40, data processing for performing image reconstruction, etc., a data collection buffer 5 for collecting data acquired in the gantry 20, a monitor 6 for displaying images, and a storage device 7 for storing therein programs, data, etc.

The table 10 comprises a cradle 12 for laying thereon the subject 40 to carry him/her into a bore in the gantry 20. The cradle 12 is vertically and horizontally translated by a motor incorporated in the table 10. As used herein, a body-axis direction of the subject 40, i.e., a direction of horizontal translation of the cradle 12, will be referred to as z-axis direction, a vertical direction as y-axis direction, and a horizontal direction perpendicular to the z- and y-axis directions as x-axis direction.

The gantry 20 comprises a rotatably supported rotating section 15. The rotating section 15 is provided with an X-ray tube 21, an X-ray controller 22 for controlling the X-ray tube 21, an aperture 23 for shaping X-rays 81 emanating from the X-ray tube 21 into a fan beam or a cone beam, an X-ray detector 24 for detecting the X-rays 81 passing through the subject 40, a DAS 25 for collecting output signals from the X-ray detector 24 as data, and a rotating section controller 26 for controlling the X-ray controller 22 and aperture 23. The body of the gantry 20 comprises a master controller 29 for communicating control signals and the like with the operation console 1 and table 10. The rotating section 15 and the body of the gantry 20 are electrically connected to each other via a slip ring 30. The rotating section 15 is capable of rotating at a velocity of rotation (rotation time) of 0.35 seconds/rotation at maximum.

The X-ray tube 21 and X-ray detector 24 are placed facing each other on either side of an imaging volume in which the subject 40 is placed, i.e., the bore of the gantry 20. A rotation of the rotating section 15 causes the X-ray tube 21 and X-ray detector 24 to rotate around the subject 40 while keeping their positional relationship. The X-rays 81 in the form of a fan or cone beam emitted from the X-ray tube 21 and shaped through the aperture 23 pass through the subject 40 and impinge upon a detecting surface of the X-ray detector 24.

In the description here, a direction of width of the fan- or cone-beam X-rays 81 in the xy plane will be referred to as channel direction, an angle of the width as fan beam angle α, and a direction of width in the z-axis direction or the z-axis direction itself as slice direction.

The X-ray detector 24 is comprised of a plurality of detector elements $24i$ disposed in the channel and slice directions. The number of the detector elements $24i$ in the channel direction is of the order of 1000 over a 60-degree angular range, for example, and they are arranged in 64 rows in the slice direction at a pitch of the order of 1 mm, for example. The coverage of the X-ray detector 24 is 40 mm.

The subject 40 is attached with a heart rate monitor 51. The heart rate monitor 51 is, for example, an electrocardiograph for acquiring an electrocardiogram. The heart rate monitor 51 measures a heartbeat waveform H of the heart of the subject 40, and transmits signals thereof to the X-ray CT apparatus 100. The X-ray CT apparatus 100 receives the signals to monitor the heartbeat waveform H of the heart of the subject 40 nearly in real time.

Next, a functional configuration of cardiac-gated imaging-related sections in the X-ray CT apparatus in accordance with the present embodiment will be described.

Figure 2:
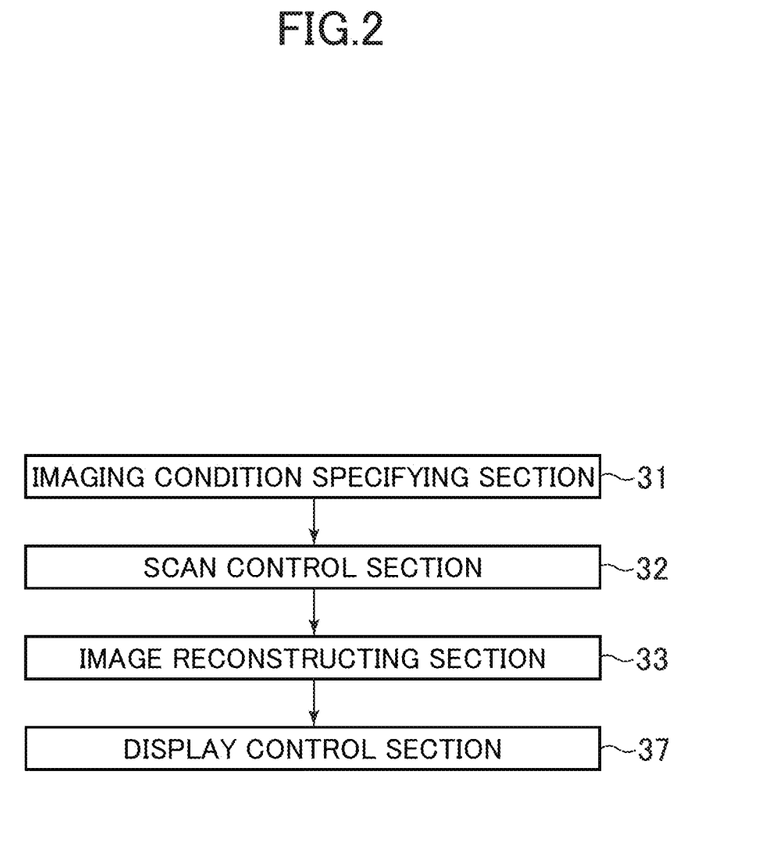
FIG. 2 is a block diagram showing a functional configuration of cardiac-gated imaging-related sections in the X-ray CT apparatus in accordance with the embodiment of the invention.

FIG. 2 is a block diagram showing a functional configuration of cardiac-gated imaging-related sections in the X-ray CT apparatus in accordance with the present embodiment. As shown in FIG. 2, the X-ray CT apparatus 100 has an imaging condition specifying section 31, a scan control section 32, an image reconstructing section 33, and a display control section 37. It should be noted that these sections are functionally implemented by the data processing apparatus 3 loading programs stored in the storage device 7 and executing them. Now functions of these sections will be described hereinbelow.

The imaging condition specifying section 31 specifies imaging conditions in response to an operation by the operator 41.

The scan control section 32 controls the data collection system comprising the table 10 and gantry 20 to perform a scan for cardiac-gated imaging on the subject 40 based on the specified imaging conditions. By performing the scan, scan data i.e., projection data, are collected in a plurality of views.

The image reconstructing section 33 reconstructs an image based on the scan data collected by the scan. The image reconstruction is achieved by using a three-dimensional back-projection method, for example.

The display control section 37 controls the monitor 6 to display a reconstructed image and information such as text on its screen.

Next, flow of processing for cardiac-gated imaging executed in the X-ray CT apparatus in accordance with the present embodiment will be described.

Figure 3:
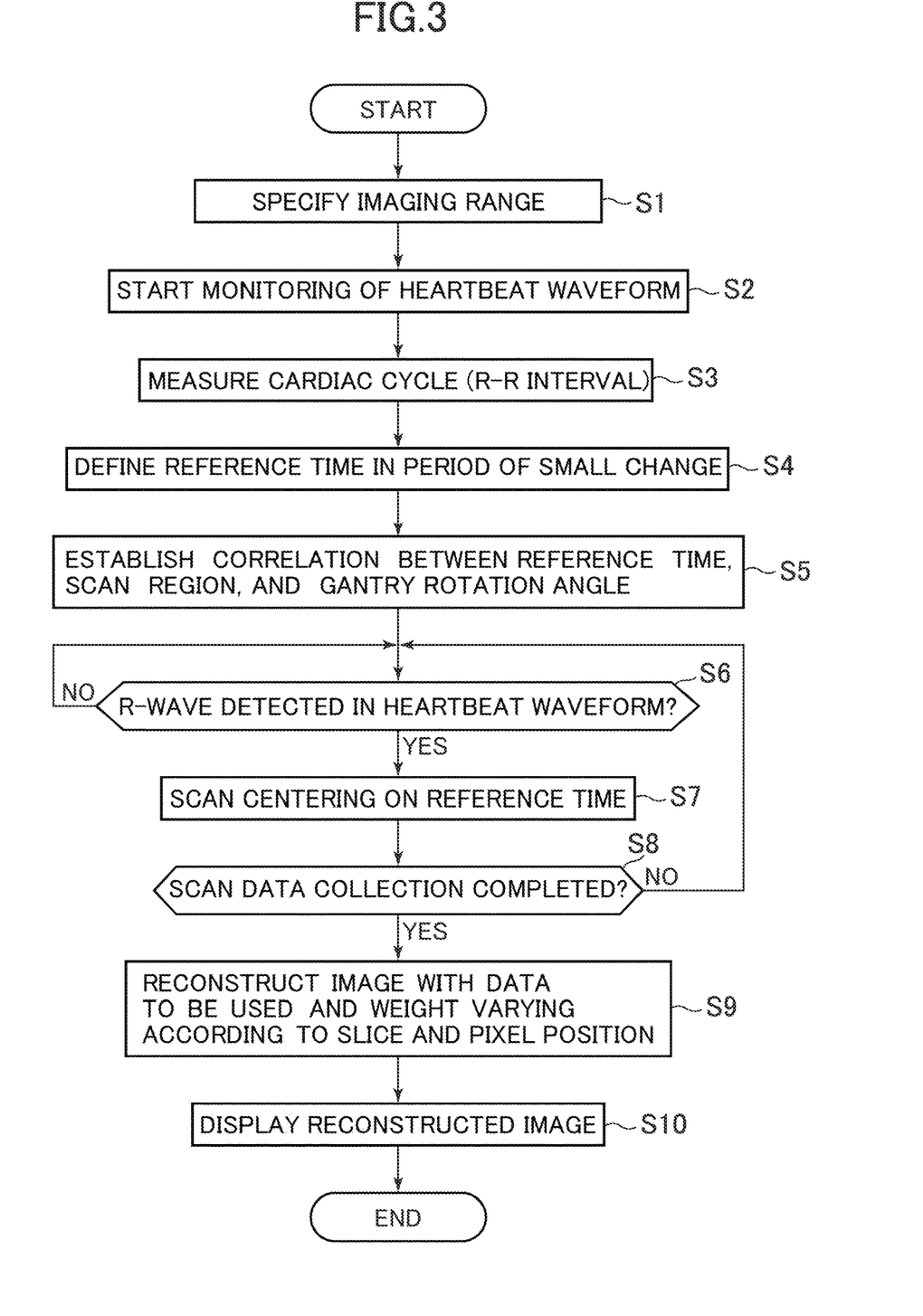
FIG. 3 is a flow chart showing flow of cardiac-gated imaging in accordance with the embodiment of the invention.

FIG. 3 is a flow chart showing flow of cardiac-gated imaging in accordance with the present embodiment.

At Step S1, imaging conditions are specified in response to an operation by the operator 41. The imaging conditions include a velocity of gantry rotation V, and an imaging range SR for the subject 40 in the z-axis direction. In the example here, the velocity of gantry rotation V is assumed to be 0.35 seconds/rotation, and the imaging range SR is assumed to be a range of the order of 150 mm including the heart.

At Step S2, monitoring of a heartbeat waveform H is started using the heart rate monitor 51.

At Step S3, a cardiac cycle T is measured based on the monitored heartbeat waveform H. For example, a time interval between the latest two adjacent R-waves in the heartbeat waveform H is calculated as cardiac cycle T. An average of the time interval between two adjacent R-waves may be calculated as cardiac cycle T.

At Step S4, a reference time tm associated with a scan is defined in a period E of small change in the cardiac phase during one cardiac cycle T. The period E of small change is a period of time in which motion of the heart is relatively small within one cardiac cycle T, for example, diastole of the heart. The diastole of the heart generally falls within a range of 50- to 90-% cardiac phase after an R-wave in the heartbeat waveform H. The reference time tm is also a time serving as reference of a data collection period K for collecting scan data over a gantry rotation angle, i.e., view angle, required in image reconstruction. Since a half scan technique is employed in the present example, the reference time tm serves as reference of a data collection period for collecting scan data over a view angle range of 180 degrees equivalent to a half scan plus an X-ray fan beam angle α. It should be noted that the X-ray fan beam angle will be sometimes referred to simply as "fan angle."

At Step S5, correlation is established between one scan performed with reference to the defined reference time, a scan region thereof, and a gantry rotation angle (view angle). Now this will be described in detail.

Figure 4:
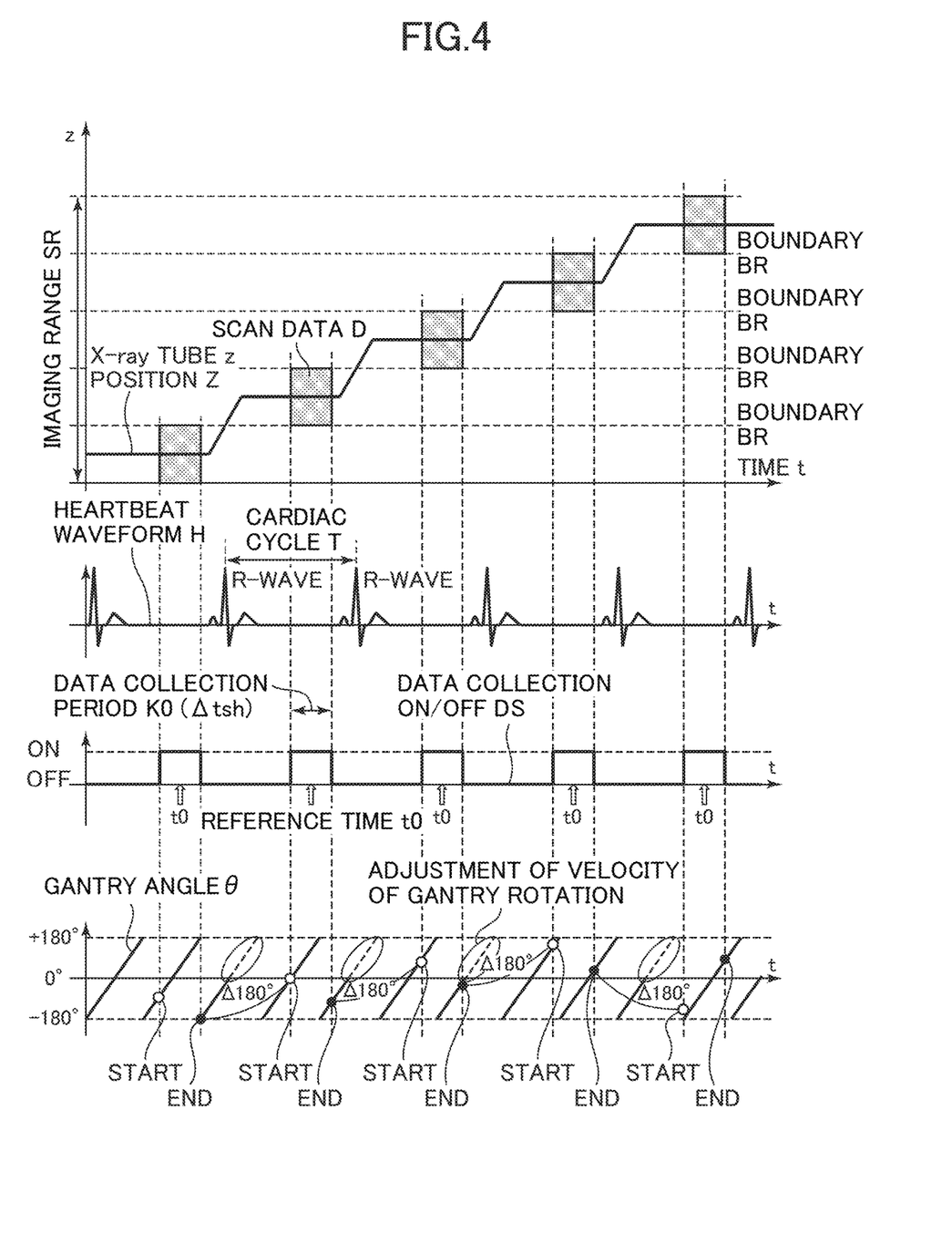
FIG. 4 shows a first example of a timing chart for cardiac-gated imaging in accordance with the embodiment of the invention.
Figure 5:
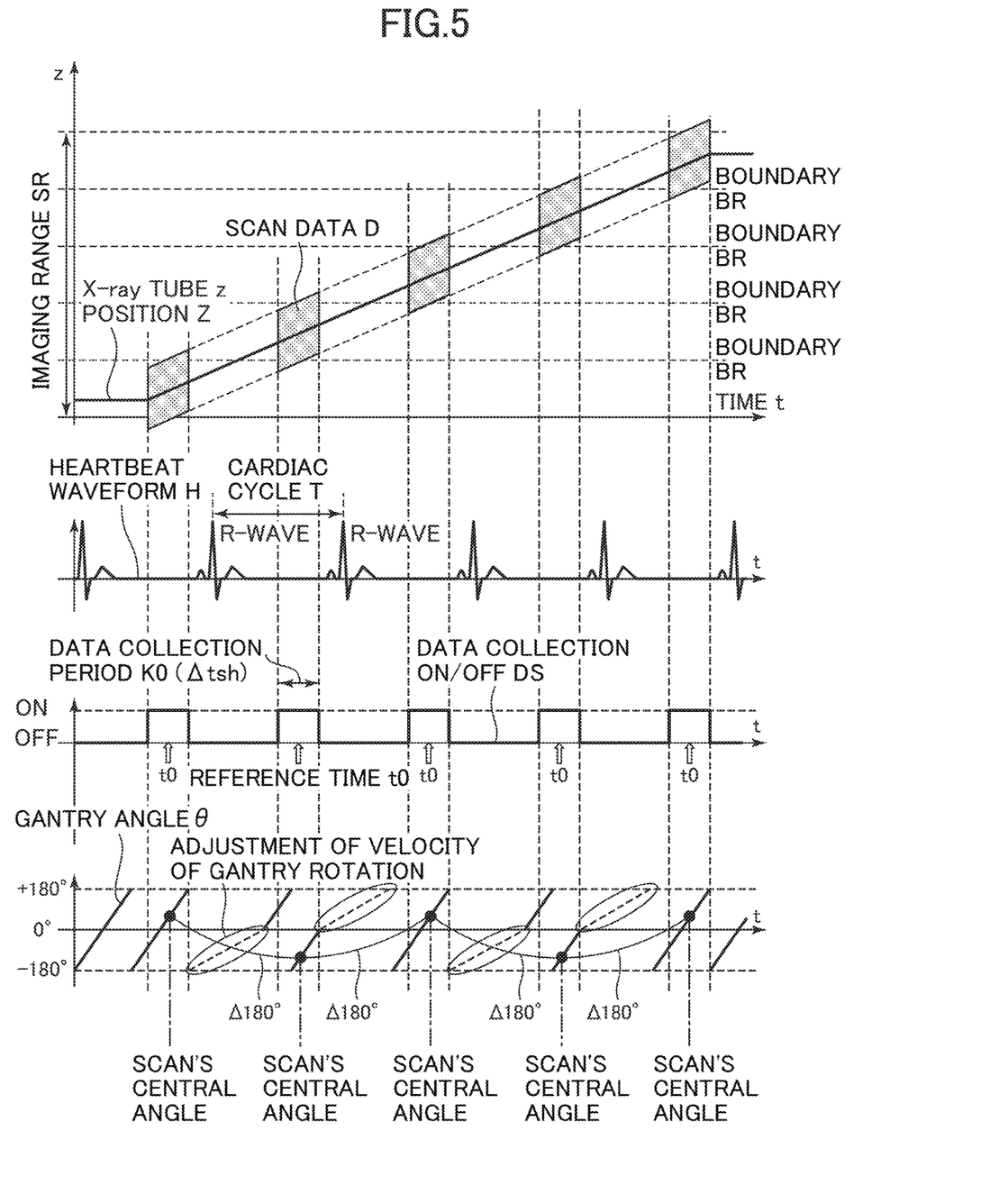
FIG. 5 shows a second example of a timing chart for cardiac-gated imaging in accordance with the embodiment of the invention.

FIGS. 4 and 5 are exemplary timing charts of cardiac-gated imaging in accordance with the present embodiment. FIG. 4 shows a case in which an axial scan is performed, and FIG. 5 shows another in which a helical scan is performed. These charts define time t along a horizontal axis, and represent the time of collection of scan data D used in image reconstruction for each slice within the imaging range SR, the heartbeat waveform H, the reference time t0 for data collection, the position Z in the z-axis direction of the X-ray tube 21 relative to the table 10, the gantry angle θ representing the position of the rotation angle of the X-ray tube 21, and turning on/off DS of data collection.

As shown in FIGS. 4 and 5, at Step S5, the whole imaging range SR including the heart is to be scanned by scans for a plurality N of heartbeats, and scan regions respectively covered by the first through N-th scans are determined. It should be noted that the scan regions for the scans are arranged so that they are adjacent to or partially overlap one another in the z-axis direction. Moreover, one scan (for one heartbeat) with reference to the reference time t0 may be an axial scan or a helical scan, provided that for a helical scan, the helical pitch is set to be low, for example 0.2 or lower.

Further, as shown in FIGS. 4 and 5, at Step S5, the gantry rotation angle, i.e., view angle (rotation angle of the X-ray tube 21), θ in a scan is defined so that the central angle of the view angle range in an i-th scan and that in a next (i+1)-th scan are substantially offset by 180 degrees. Specifically, for every pair of two adjacent scans, control is made so that the gantry rotation angle θ centered in the view angle range for collecting scan data is offset by 180 degrees between one scan and a next scan. Such control achieves a positional relationship by which the view angle range for scan data to be collected may complement a missing cone in each scan. Consequently, cone-beam artifacts may be suppressed during image reconstruction, and boundary artifacts may be suppressed by reducing a discontinuous factor in the z-axis direction in a reconstructed image.

At Step S6, processing for detecting the latest R-wave in the monitored heartbeat waveform H is performed, and a decision is made as to whether the R-wave is detected or not. In the case that the R-wave is detected, the process goes to Step S7. In the case that no R-wave is detected, the process goes back to Step S6.

At Step S7, after detecting the R-wave, an axial scan is performed in a data collection period associated with a reference time t1. The axial scan is a half scan for collecting scan data in a view angle range of 180 degrees plus a fan beam angle α as data for image reconstruction for one slice.

The axial scan is performed on a scan region determined according to what number the current scan is based on the correlation determined at Step S5. At that time, the scan is performed so that the gantry rotation angle centered in the view angle range for collecting scan data is substantially offset by 180 degrees between adjacent scans, that is, one scan and a next scan. The control for this is achieved by controlling the velocity of gantry rotation or translation of the table 10 based on the measured heartbeat waveform H, cardiac cycle T, coverage of the X-ray detector 24, and the like.

At Step S8, a decision is made as to whether scan data for the whole imaging range SR have been collected or not. When collected, the process goes to Step S9. When not collected, the process goes back to Step S6.

Figure 6:
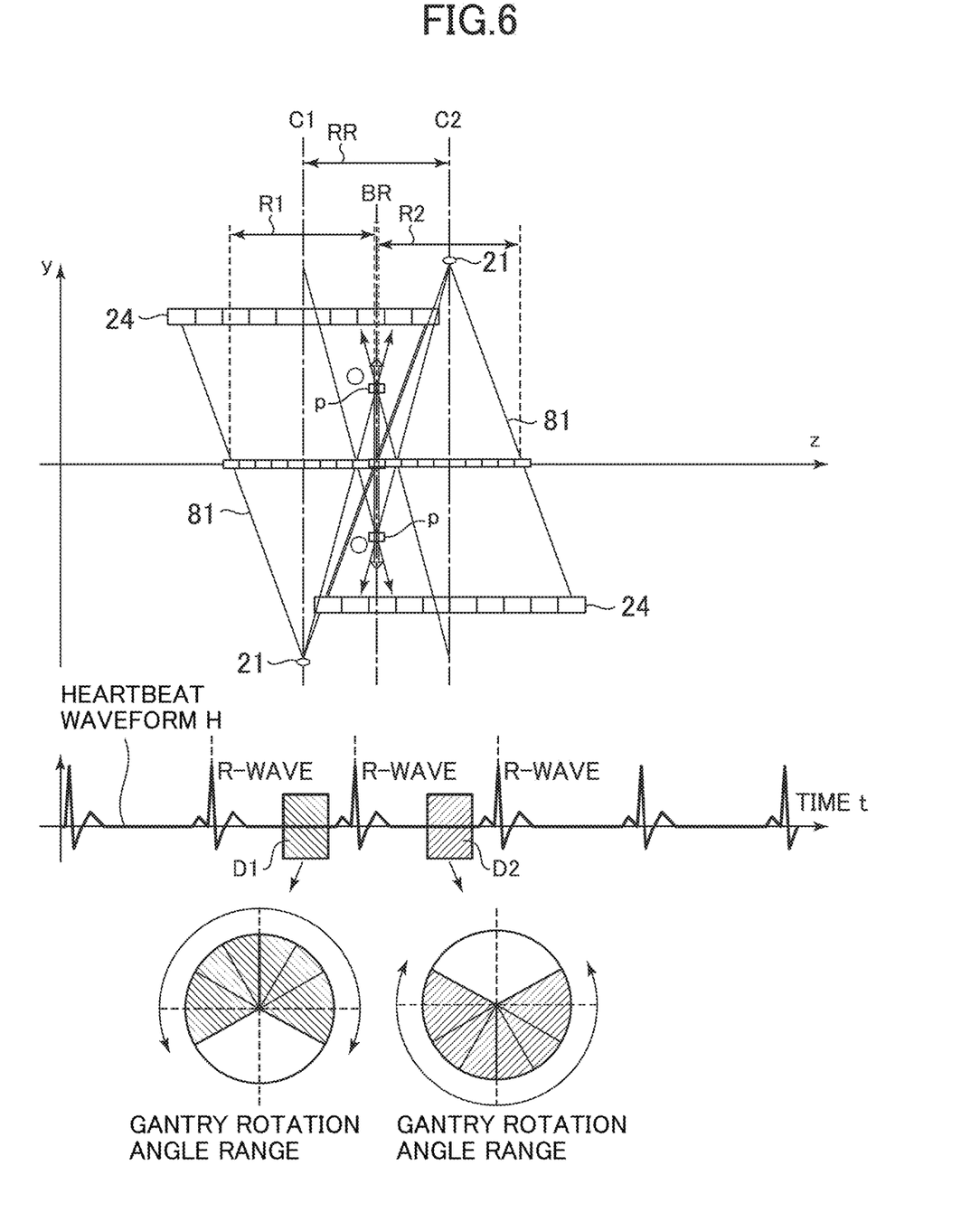
FIG. 6 is a diagram for explaining image reconstruction in accordance with the embodiment of the invention.

At Step S9, image reconstruction is performed for each slice in the imaging range SR based on the collected scan data. For slices in the outer half of the scan region on either side among a plurality of scan regions arranged in the z-axis direction and assigned to the imaging range SR, their images are reconstructed using only scan data acquired by respective scans on the scan regions. For slices in the other region, their images are reconstructed by the method as follows:

FIG. 6 is a diagram for explaining image reconstruction in accordance with the present embodiment.

As shown in FIG. 6, here, scan regions adjacent to each other in the z-axis direction are represented as first scan region R1 and second scan region R2, the center of the first scan region R1 as first scan center position (first position) C1, and the center of the second scan region R2 as second scan center position (second position) C2. Moreover, a region RR is defined as a region of interest, which lies between the first scan center position C1 and second scan center position C2, and includes a position in the middle of the first scan center position C1 and second scan center position C2, i.e., a virtual border BR between the first scan region R1 and second scan region R2. Now an image corresponding to a slice at each position within the region RR of interest is reconstructed using the first and second scan data D1, D2. At that time, depending upon the position of the current slice relative to the first and second scans center positions C1, C2, a view-angle-range-based use rate a for the first scan data D1 and a view-angle-range-based use rate b for the second scan data D2 are determined. For example, in the case that the view angle range for the scan data is 240 degrees, which is 180 degrees plus a fan beam angle of 60 degrees, data over the 240 degrees are used when the use rate is 100%, while data over the 120 degrees are used when the use rate is 50%. The method of determining the use rates a, b is as follows, for example: the view-angle-range-based use rate a for the first scan data D1 is set to 100% when the position of the slice falls within the first scan region R1, and the view-angle-range-based use rate b for the second scan data D2 is lowered for a slice position closer to the first scan center position C1. Moreover, the view-angle-range-based use rate b for the second scan data D2 is set to 100% when the position of the slice falls within the second scan region R2, and the view-angle-range-based use rate a of the first scan data D1 is lowered for a slice position closer to the second scan center position C2. Now the method of setting the use rates a, b will be described by demonstrating more specific examples.

Figure 7:
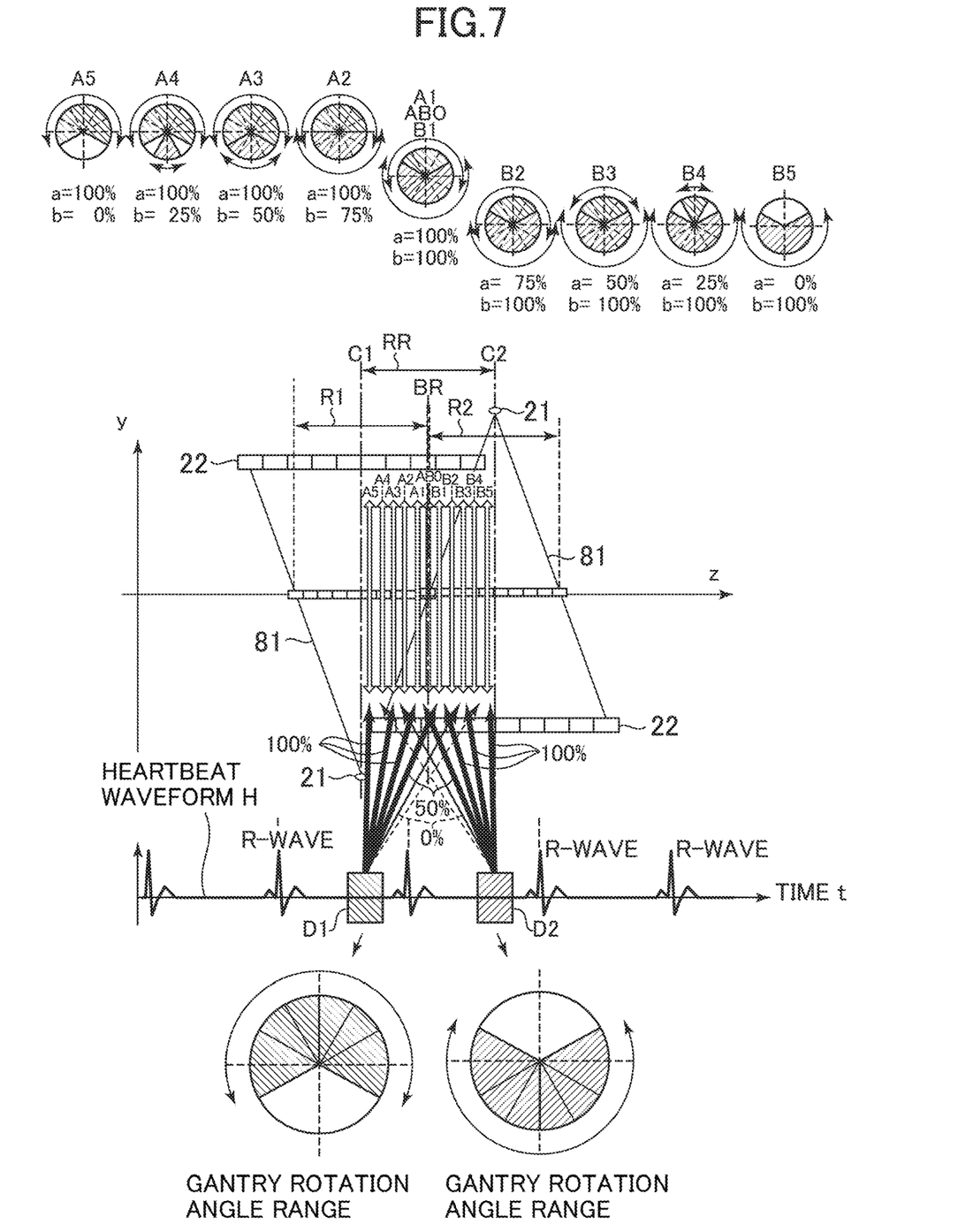
FIG. 7 is a diagram showing exemplary settings of the view-angle-range-based use rates for first and second scan data.

FIG. 7 is a diagram showing exemplary settings of the view-angle-range-based use rates for first and second scan data.

First, a slice AB0 is defined at a position of the border BR. Then, representative slices A1 to A5 are set in a region ranging from the border BR to the first scan center position C1 within the first scan region R1 sequentially from a position closest to the border BR. Similarly, representative slices B1 to B5 are set in a region ranging from the border BR to the second scan center position C2 within the second scan region R2 sequentially from a position closest to the border BR. It should be noted that the view-angle-range-based use rate a for the first scan data D1 will be referred to herein as first use rate, and the view-angle-range-based use rate b for the second scan data D2 will be referred to as second use rate.

For the first scan data D1 and second scan data D2, those centering on respective view angles opposite to each other are employed.

In slices AB0, A1, B1, the first and second use rates a, b are:
AB0: a=100%, b=100%;
A1: a=100%, b=100%; and
B1: a=100%, b=100%.
In slices A2, B2, the first and second use rates a, b are:
A2: a=100%, b=75%; and
B2: a=75%, b=100%.
Likewise, in slices A3, B3,
A3: a=100%, b=50%; and
B3: a=50%, b=100%,
in slices A4, B4,
A4: a=100%, b=25%; and
B4: a=25%, b=100%, and
in slices A5, B5,
A5: a=100%, b=0%; and
B5: a=0%, b=100%.

Since slices A3 to B3 can hold 360 degrees of view angle range, what is commonly called full scan reconstruction is performed for these slices, in which reconstruction is performed using scan data over a view angle range of 360 degrees.

While the description here is made with reference to an example in which the number of slices is small and the change of the view-angle-range-based use rates a, b for the first and second scan data D1, D2 is in increments of 25% for simplifying the explanation, the number of slices is larger and the use rates are continuously changed in finer increments in practice. Thus, artifacts due to discontinuous boundaries may be reduced by continuously changing images centering on an image in the vicinity of the virtual border BR between the first scan region R1 and second scan region R2 toward images away from the vicinity of the border. Moreover, since the processing mixes complementary scan data together so that insufficiency of conjugate data due to a missing cone is complemented, rather than simply mixing images, and then reconstructs images based on the scan data, the images are less susceptible to what is commonly called blurring.

Furthermore, in reconstructing each pixel in the reconstruction plane by back-projection of scan data i.e., projection data here, weighting is applied to conjugate data whose X-ray paths pass through that pixel. The weighting is applied according to the cone angle of the X-ray path, i.e., angle of the X-ray path with respect to the reconstruction plane. In general, the weight to be multiplied with projection data for an X-ray path is set to be smaller for a larger cone angle of the X-ray path, and is set to be larger for a smaller cone angle of the X-ray path. This is done for the purpose of increasing the contribution ratio of projection data whose X-ray path has a smaller angle formed with the reconstruction plane because the value of the pixel to be reconstructed may be determined with higher precision in principle for an X-ray path of projection data to be back-projected lying in a direction more parallel to the reconstruction plane. Now a specific example of weighting on projection data will be described with reference to the drawings.

Figure 8:
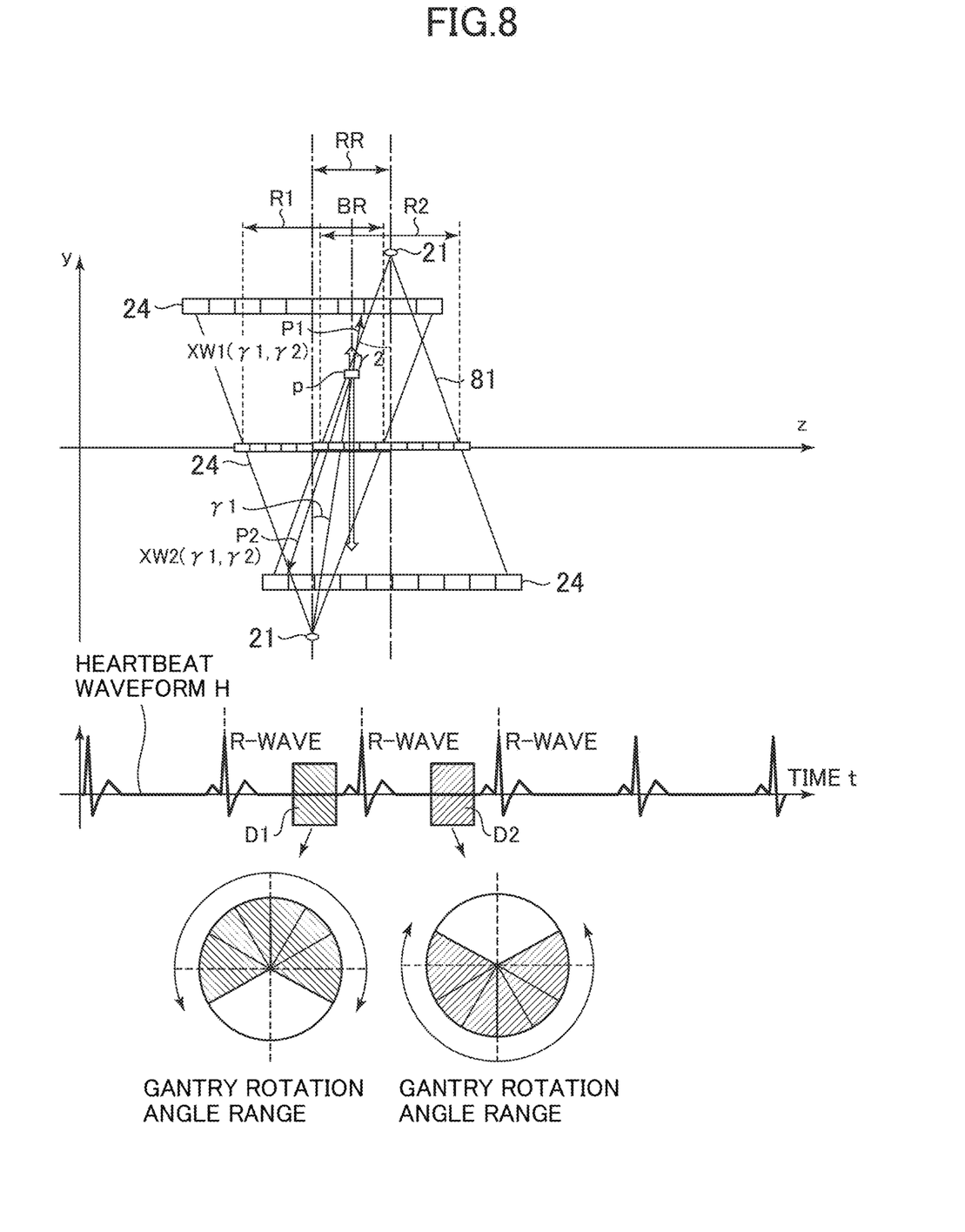
FIG. 8 is a diagram showing geometry of a data collection system for a relatively large overlapping region between the first scan region and second scan region that are adjacent to each other.
Figure 9:
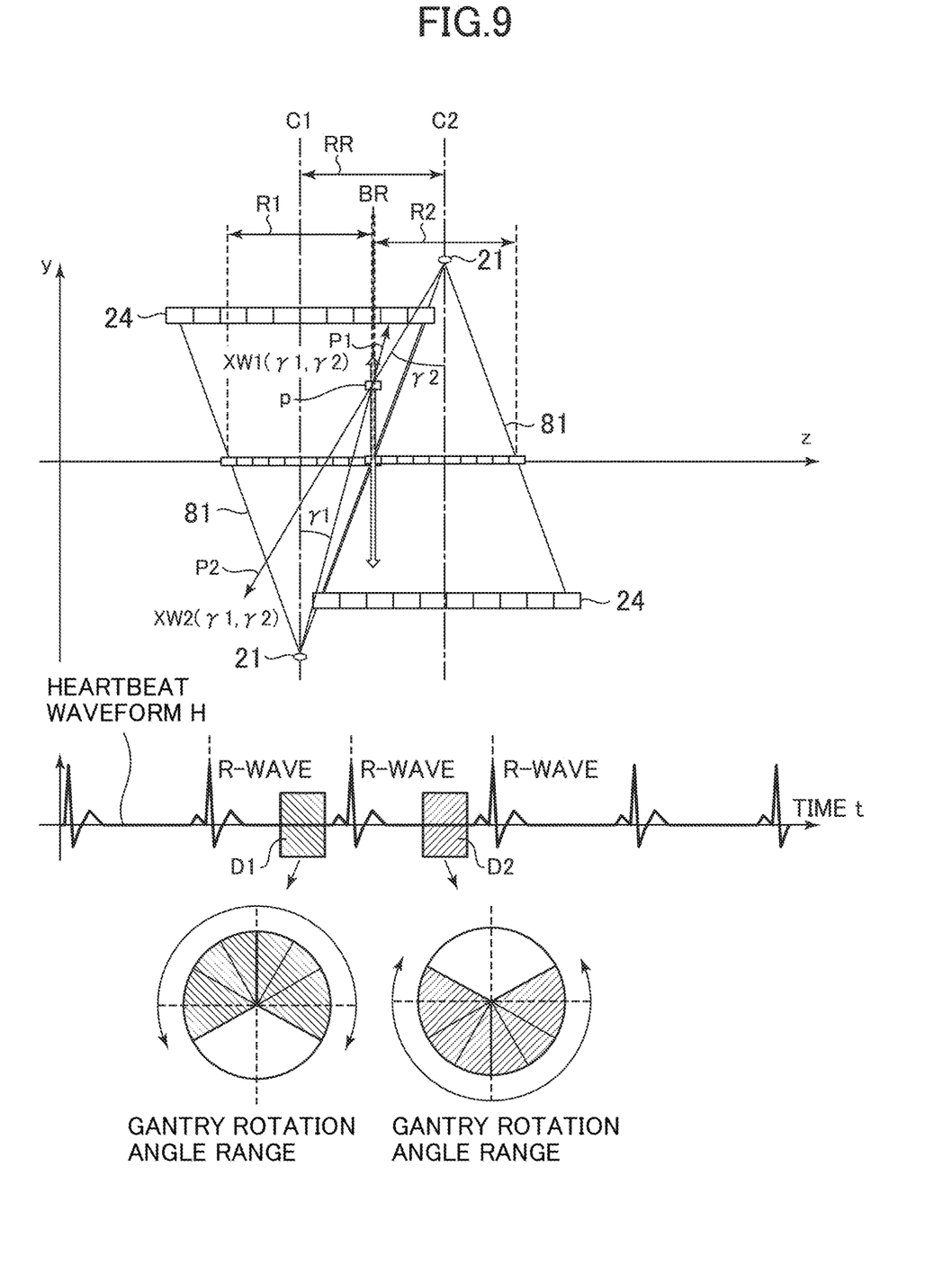
FIG. 9 is a diagram showing geometry of the data collection system for a relatively small overlapping region between the first scan region and second scan region that are adjacent to each other.

FIG. 8 is a diagram showing geometry of the data collection system for a relatively large overlapping region between the first scan region R1 and second scan region R2 that are adjacent to each other. FIG. 9 is a diagram showing geometry of the data collection system for a relatively small overlapping region between the first scan region R1 and second scan region R2 that are adjacent to each other.

Referring to these geometries shown in the drawings, let us consider a case in which a pixel p in a reconstruction plane of the slice AB0 lying on a virtual border, i.e., in the middle, of the first scan center position C1 and second scan center position C2 is reconstructed. As shown in FIG. 8, for a larger overlapping region between the first scan region R1 and second scan region R2, conjugate data whose X-ray paths pass through the pixel p are constructed from measured data in a scan on the first scan region R1 and measured data in a scan on the second scan region R2. As shown in FIG. 9, for a smaller overlapping region between the first scan region R1 and second scan region R2, conjugate data whose X-ray paths pass through the pixel p are constructed from extrapolated data obtained by extrapolation on the measured data in a scan on the first scan region R1 and measured data in a scan on the second scan region R2. In either case, conjugate data of the pixel p not lying at the center of a reconstruction plane are constructed from projection data P1 whose X-ray path has a relatively small cone angle of $\gamma 1$ and projection data P2 whose X-ray path has a relatively large cone angle of $\gamma 2$. In this case, a weight W1 for the projection data P1 is set to be relatively large and a weight W2 for the projection data P2 is set to be relatively small. As an example, weight $W1(\gamma 1, \gamma 2)=\gamma 2 \times \gamma 2/(\gamma 1 \times \gamma 1 + \gamma 2 \times \gamma 2)$, and weight $W2(\gamma 1, \gamma 2)=\gamma 1 \times \gamma 1/(\gamma 1 \times \gamma 1 + \gamma 2 \times \gamma 2)$.

At Step S10, a reconstructed image is displayed. For example, an MPR image in a three-dimensional image obtained by stacking the images of the slices in the imaging range SR in the z-axis direction is produced for display on a screen.

According to the embodiment above, an image corresponding to a slice lying at each position within a region including a virtual border BR between the first scan region R1 and second scan region R2 that are adjacent each other in the z-axis direction is reconstructed using first and second scan data D1, D2, and at that time, the view-angle-range-based use rate a for the first scan data D1 in and the view-angle-range-based use rate b for the second scan data D2 are determined according to the position of that slice relative to the first and second scan center positions C1, C2. For example, when the position of the slice falls within the first scan region R1, the view-angle-range-based use rate a for the first scan data D1 is set to 100%, and the view-angle-range-based use rate b for the second scan data D2 is lowered for a slice position closer to the first scan center position C1. On the other hand, when the position of the slice falls within the second scan region R2, the view-angle-range-based use rate b for the second scan data D2 is set to 100%, and the view-angle-range-based use rate a for the first scan data D1 is lowered for a slice position closer to the second scan center position C2. Thus, images can be continuously changed centering on an image at the border between the first scan region R1 and second scan region R2 toward images away from the border to reduce artifacts due to discontinuous boundaries. Moreover, since the processing mixes complementary scan data together so that insufficiency of scan data due to a missing cone is complemented, rather than simply mixing images, and then reconstructs an image based on the scan data, the images are less susceptible to what is commonly called blurring.

Moreover, according to the embodiment above, for every pair of two scans whose scan regions are adjacent to each other, control is made so that the central angle of a view angle range for collecting scan data is substantially offset by 180 degrees between one scan and a next scan, whereby a positional relationship by which a view angle range of scan data to be collected may complement a missing cone in each scan may be achieved. Consequently, cone-beam artifacts may be suppressed during image reconstruction, and boundary artifacts may be suppressed by reducing a discontinuous factor in the z-axis direction in a reconstructed image.

Furthermore, according to the embodiment above, in reconstructing each pixel in a reconstruction plane by back-projection of scan data (projection data), weighting is applied to conjugate data whose X-ray paths pass through that pixel. In the weighting, the weight to be multiplied with projection data for an X-ray path is set to be smaller for a larger cone angle of the X-ray path, and is set to be larger for a smaller cone angle of the X-ray path. Thus, by increasing the contribution ratio of projection data for smaller angle formed between the X-ray path and reconstruction plane, the value of the pixel to be reconstructed can be determined with higher precision.

The invention is not limited to the embodiment above and may be practiced in several variations without departing from the spirit and scope of the invention.

For example, the timing charts of cardiac-gated imaging in accordance with the embodiment above are provided merely by way of example, and control of rotation of the gantry 20 and/or translation of the table 10 may take any one of a variety of patterns. In other words, the velocity of rotation of the gantry 20 and the velocity of translation of the table 10 may be variable.

Moreover, for example, while in the embodiment above, control is made so that the central angle of a view angle range for collecting scan data is substantially offset by 180 degrees between one scan and a next scan, the offset amount is not limited to 180 degrees, and may be only slight. Any offset amount, as compared with no offset amount, can increase the amount of scan data that can complement the other. Therefore, mere "control for deliberately offsetting" the gantry rotation angle between one scan and a next scan may be somewhat effective, and additionally, "control for bringing the offset amount closer to 180 degrees" may be more effective.

Furthermore, for example, a program for causing a computer to function as several sections in such an X-ray CT apparatus 100, and a computer-readable storage medium in which the program is stored also constitute exemplary embodiments of the invention.

In addition, for example, while the embodiment above refers to an X-ray CT apparatus, the invention may be applied to a PET-CT or SPECT-CT apparatus in which an X-ray CT apparatus is combined with PET (Positron Emission Tomography) or SPECT (Single Photon Emission Computed Tomography).

What is claimed is:

1. A radiation tomography apparatus for performing cardiac-gated imaging on a subject using a data collection system comprising a radiation source and a detector rotating around said subject, said radiation tomography apparatus comprising:
   a master controller including a scan control section for controlling said data collection system to acquire first scan data by a first scan for scanning a first scan region centering on a first position of said subject in a body axis direction in synchronization with heartbeats of said subject, and acquire second scan data by a second scan for scanning a second scan region adjacent to or partially overlapping said first scan region and centering on a second position of said subject in a body axis direction in synchronization with heartbeats of said subject; and
   a data processing apparatus including a reconstructing section for reconstructing an image corresponding to a slice between said first position and said second position using said first and second scan data, said reconstructing section determining a view-angle-range-based use rate for said first scan data and a view-angle-range-based use rate for said second scan data according to a position of said slice relative to said first and second positions;
   wherein said reconstructing section lowers the view-angle-range-based use rate for said second scan data for a position of said slice closer to said first position, and lowers the view-angle-range-based use rate for said first scan data for a position of said slice closer to said second position; and
   wherein when the view-angle-range-based use rate for said first scan data or the second scan data is lower than 100%, data over a part of a view angle range corresponding to the first scan data or the second scan data, respectively, is used to reconstruct the image, but data over the other part of the view angle range is not used to reconstruct the image.

2. The radiation tomography apparatus as recited in claim 1, wherein said reconstructing section, when reconstructing a pixel in a reconstruction plane of said slice by back-projecting scan data for a radiation path passing through said pixel, changes a weight of said scan data according to an angle of said radiation path with respect to said reconstruction plane.

3. The radiation tomography apparatus as recited in claim 2, wherein said reconstructing section increases the weight of scan data for said radiation path for a smaller angle of said radiation path with respect to said reconstruction plane, and decreases the weight of the scan data for said radiation path for a larger said angle.

4. The radiation tomography apparatus as recited in claim 1, wherein said first and second scans each acquire scan data in a view angle range of 180 degrees plus a radiation fan beam angle; and said scan control section controls said data collection system so that a difference between a central angle of the view angle range in said first scan and a central angle of the view angle range in said second scan is from 90 to 180 degrees.

5. The radiation tomography apparatus as recited in claim 4, wherein said scan control section controls said data collection system so that said difference is 180 degrees.

6. The radiation tomography apparatus as recited in claim 5, wherein said reconstructing section reconstructs an image corresponding to said slice using scan data in a view angle range of 360 degrees.

7. The radiation tomography apparatus as recited in claim 1, wherein when the position of the slice falls within the first scan region, the view-angle-range-based use rate for the first scan data is set to 100%.

8. The radiation tomography apparatus as recited in claim 1, wherein when the position of the slice falls within the second scan region, the view-angle-range-based use rate for the second scan data is set to 100%.

9. A non-transitory computer-readable medium storing a program that, when executed by a computer, causes the computer to generate signals to:
   control a data collection system of a radiation tomography apparatus to acquire first scan data by a first scan for scanning a first scan region centering on a first position of a subject in a body axis direction in synchronization with heartbeats of said subject, and to acquire second scan data by a second scan for scanning a second scan region adjacent to or partially overlapping said first scan region and centering on a second position of said subject in a body axis direction in synchronization with heartbeats of said subject; and reconstruct an image corresponding to a slice between said first position and said second position using said first and second scan data, and to determine a view-angle-range-based use rate for said first scan data and a view-angle-range-based use rate for said second scan data according to a position of said slice relative to said first and second positions;

wherein said first position of said first scan is 180 degrees from said second position of said second scan; and wherein when the view-angle-range-based use rate for said first scan data or the second scan data is lower than 100%, data over a part of a view angle range corresponding to the first scan data or the second scan data, respectively, is used to reconstruct the image, but data over the other part of the view angle range is not used to reconstruct the image.

* * * * *